United States Patent [19]

Adler et al.

[11] Patent Number: 4,758,562
[45] Date of Patent: Jul. 19, 1988

[54] METHOD FOR INDUCING HYPOTHERMIA AND/OR POIKILOTHERMIA

[75] Inventors: Martin W. Adler, Dresher; Ellen B. Geller, Philadelphia, both of Pa.

[73] Assignee: Temple University of the Commonwealth System of Higher Education, Philadelphia, Pa.

[21] Appl. No.: 810,969

[22] Filed: Dec. 18, 1985

[51] Int. Cl.[4] .................... A61K 31/40; A61K 31/44; A61K 31/54

[52] U.S. Cl. ................................ 514/224.8; 514/282; 514/408; 514/409; 514/225.5; 514/225.8

[58] Field of Search ................ 514/223, 282, 408, 409

[56] References Cited

PUBLICATIONS

Chem. Abst., 85-153867t (1976).
Lahti et al., *Properties of a Selective Kappa Agonist, U-50,488H*, Life Sciences, vol. 31, pp. 2257-2260, 1982.
Vonvoigtlander et al. *U-50,488: A Selective and Structurally Novel Non-Mu(Kappa) Opioid Agonist*, The Journal of Pharmacology and Experimental Therapeutics, vol. 224, No. 1, pp. 7-12, 1983.
Piercey et al., *U-50488 H, A Pure Kappa Receptor Agonist with Spinal Analgesic Loci in the Mouse*, Life Sciences, vol. 31, pp. 1197-1200, 1982.
Lahti et al., *[3H] U-69593 A highly Selective Ligand for the Opioid K Receptor*, European Journal of Pharmacology, 109, pp. 281 to 284, 1985.
Vonvoigtlander et al., *Kappa Opioid Analgesia is Dependent on Serotonergic Mechanisms*, The Journal of Pharmacology and Experimental Therapeutics, vol. 231, No. 2, pp. 270 to 274, 1984.
Shemano and Nickerson, *Effect of Ambient Temperature on Thermal Responses to Drugs*, Can. J. Biochem. Physiol., 36, pp. 1243 to 1249, 1958.
Hoffman and Zarrow, *Hypothermia in Rat, Hamster, Ground Squirrel and Pigeon Following Chlorpromazine*, Am. J. Physiol., 193, pp. 547 to 552, 1958.
Kollias and Bullard, *The Influence of Chlorpromazine on Physical and Chemical Mechanisms of Temperature Regulation in the Rat;* J. Pharmacol. Exp. Ther., 145:373-381, 1964.
Kirkpatrick and Lomax, *Temperature Changes Induced by Chlorpromazine and N-Methyl Chlorpromazine in the Rat,* Neuropharmacology 10:61-66, 1971.
Feigenbaum and Yanai, *Implications of Dopamine Agonist-Induced Hypothermia Following Increased Density of Dopamine Receptors in the Mouse*, Neuropharmacology, vol. 24, No. 8, pp. 735 to 741, 1985.
Yamawaki et al., *Dopaminergic and Serotonergic Mechanisms of Thermoregulation: Mediation of Thermal Effects of Apomorphine and Dopamine*, The Journal of Pharmacology and Experimental Therapeutics, vol. 227, No. 2, pp. 383 to 388, 1983.
Boublik and Funder, *Interaction of Dopamine Receptor Ligands with Subtypes of the Opiate Receptor*, European Journal of Pharmacology, 107, pp. 11 to 16, 1985.
Cooper et al., *Effects of Tifluadom on Food Consumption Compared with Chlordiazepoxide and Kappa Agonists in the Rat*, Neuropharmacology, vol. 24, No. 9, pp. 877 to 883, 1985.

*Primary Examiner*—Stanley J. Friedman
*Attorney, Agent, or Firm*—Seidel, Gonda, Goldhammer & Abbott

[57] ABSTRACT

A combination of drugs including a kappa opioid receptor agonist and a dopamine receptor blocker or dopamine receptor agonist provides a synergistic effect in inducing hypothermia and/or poikilothermia in humans and animals. Hypothermia as much as 10° C. at an ambient temperature of 20° C. is possible, with complete recovery and few, if any, side effects.

22 Claims, 1 Drawing Sheet

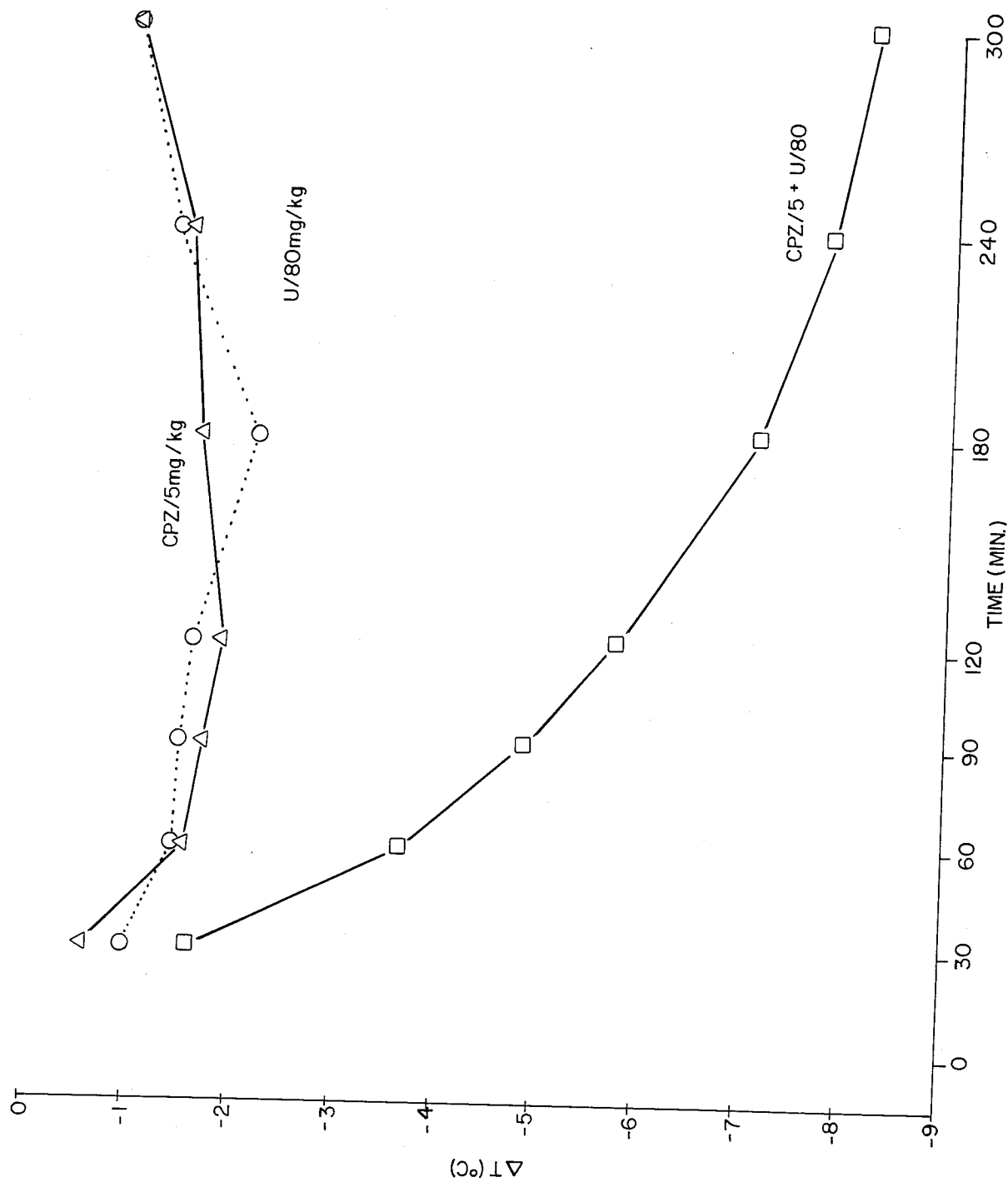

METHOD FOR INDUCING HYPOTHERMIA AND/OR POIKILOTHERMIA

This invention relates to a combination of drugs that produces hypothermia and/or poikilothermia.

This invention was supported in part by grant no. DA 00376 from the National Institute on Drug Abuse entitled "Narcotic Receptors in Nonaddicted and Addicted States".

A number of drugs are known to produce a hypothermic response when administered to man or laboratory animals. Such drugs represent a variety of drug classes including sedativehypnotics, antipsychotics, anxiolytics, opioids, and drugs that selectively affect specific neurotransmitter systems. In general, the drop in temperature achieved using such drugs is small unless large, usually toxic doses are used. As a result, potential applicability in a number of areas that might benefit from lowering of body temperature, including prolonged lowering of body temperature, has been limited.

A new combination of drugs which includes a kappa opioid receptor agonist and a dopamine receptor blocker (neuroleptic or dopamine receptor antagonist) or dopamine receptor agonist has now been found. The new drug combination of this invention provides a synergistic effect in inducing hypothermia and/or poikilothermia in humans and animals. Particularly, hypothermia and/or poikilothermia can be induced in mammals by administering thereto an effective amount of kappa opioid receptor agonist and a neuroleptic or dopamine receptor agonist or antagonist to induce hypothermia and/or poikilothermia. Preferably, a drug such as trans-3,4-dichloro-N-methyl-N-[2-(1-pyrrolidinyl)cyclohexyl]benzeneacetamide methanesulfonate (hereinafter U-50) or (5a,7a,8B)-N-methyl-N-[7-(1-pyrrolidinyl)-1-oxaspiro(4,5)-dec-8-yl]benzeneacetamide (hereinafter U-69) acting at a receptor of the opioid type in the body, the kappa receptor, in combination with a dopamine blocker, such as a neuroleptic or dopamine receptor antagonist, or dopamine receptor agonist, can produce a profound hypothermia, amounting to as much as about 10° C. at an ambient temperature of 20° C., and/or poikilothermia, in a dose-related manner, with complete recovery and few, if any, side effects.

A synergistic effect of the unique combination of drugs of this invention is shown in the Figure which compares the effect of chlorpromazine (CPZ) at 5 mg/kg dosage and U-50 (U) at 80 mg/kg dosage individually against the effect of these two drugs at the same dosage but in combination with one another. The data used in the Figure are taken from the Examples illustrating the hypothermia effect.

The hypothermia following a single administration of the drug combination of this invention lasts for about 24 hours at an ambient temperature of about 20° C. and is accomplished with complete safety and full recovery. The change in temperature can be partially reversed by a narcotic antagonist drug, such as naloxone. Subjects also appear to be made poikilothermic by the drug combination of this invention; in other words, they become unable to regulate their own body temperature which approaches the temperature of the environment. So, by lowering the ambient temperature, it is possible to increase the hypothermic effect.

While the mechanism of the invention is not completely understood, it is believed that the hypothermia effect is in fact an initial manifestation or indication of poikilothermia or of developing poikilothermia before the poikilothermia becomes the predominant effect. While there is no certain corroboration of this theory, there is no question that the unique drug combination of this invention induces both hypothermia and poikilothermia. Due to the poikilothermia, the drop in body temperature may be markedly enhanced by lowering ambient temperature. The greater the decrease in ambient temperature, the greater the decrease in body temperature.

The synergistic combination of this invention makes possible for the first time investigations into important areas of experimentation in which the lowering of body temperature, particularly over an extended period of time, could be advantageous. For example, experiments relating to artificial hibernation, especially applicable for long space voyages, and cardiac and other surgical procedures that are complex, traumatic, risky and not easily reversed are now possible. Limitations on current methodologies include atrial fibrillation, increased $pCO_2$ and decreased pH of the blood. In addition, in near-drowning syndrome it is often necessary to return the body temperature to normal gradually. Available procedures for maintaining hypothermia for day-long or longer periods use primarily physical means such as ice packs or barbiturate anesthesia, which are difficult to regulate and potentially dangerous. As an adjunct to chemotherapy for cancer treatment, the slowing of metabolism by marked lowering of body temperature should avoid the nausea, vomiting and many other side-effects of chemotherapy. The invention could also provide a safer more effective treatment for malignant hyperthermia than dantrolene, the drug now used to treat this condition. In addition, maintenance of lowered body temperature may benefit a patient suffering from a stroke by protecting the brain and spinal cord from further injury following the incident. A further advantage of the poikilothermia induced by the unique drug combination of this invention for a physician is that he or she does not have to be concerned that the body of the patient will thwart treatment efforts by attempting to regulate its own temperature. The physician can control the body temperature completely and safely by controlling the ambient temperature.

Opioids such as morphine are known to alter body temperature. The precise effect is a consequence of a number of variables, but morphine generally produces a dual response when administered to rats by a parenteral route: a low dose hyperthermia and a high dose hypothermia. Antipsychotics such as chlorpromazine are known to produce a fall in body temperature in rates, generally in the range of 2° or 3° C. at normal ambient temperatures unless large doses, above about 10 mg/kg, are administered. However, when the combination of drugs of this invention is used, profound hypothermia at an ambient temperature of 20° C. is produced. The effect is long-lasting, completely without lethality at normal ambient temperatures, and is antagonized by naloxone.

Any kappa opioid receptor agonist or mixture of kappa opioid agonists which will produce a drop in body temperature ranging from 0.0° C. to 6.0° C. at normal ambient temperature (20°–25° C.) over the full range of dosages from the lowest (no activity) to high dosage amounts can be used in the practice of this invention. Examples of such drugs include bremazocine, nalorphine, ketazocine, including alkyl ketazocines such as ethylketazocine, tifluadom, trans-3,4-dichloro- N-methyl-N-[2-(1-pyrrolidinyl)cyclohexyl]benzeneacetamide, (5a,7a,8B)-N-methyl-N-[7-(1-pyrrolidinyl)-1-oxaspiro(4,5)-dec-8-yl]benzeneacetamide and the like, with the latter two drugs preferred. More preferred are salts of the kappa opioid agonists. The salts generally facilitate the activity of the drug by increasing its solubility, particularly in lipids and aqueous media, and increasing the duration of action. Any suitable salt of any of the kappa opioid agonists can be used. Some such suitable salts that may be employed include the hydrochloride, methanesulfonate, besylate, maleate, decanoate, enanthate, succinate, lactate, sulfate, quaternary ammonium and any other salt grouping that might be selected by one of ordinary skill in the art. Some specific examples of salts of kappa opioid receptor agonists include bremazocine hydrochloride, nalorphine hydrochloride, ketazocine salts including alkyl ketazocine methanesulfonates such as ethyl ketazocine methanesulfonate, trans-3,4-dichloro-N-methyl-N-[2-(1-pyrrolidinyl)cyclohexyl]benzeneacetamide methanesulfonate, and the like and mixtures thereof.

Any dopamine receptor blocker, i.e. neuroleptic or dopamine receptor antagonist, or mixtures thereof can be used in the practice of this invention. Phenothiazines, particularly those containing aliphatic, piperidine, and piperazine groups, combinations of them and the like can be used as well as mixtures thereof. Generally, any compound containing the characteristic phenothiazine nucleus or core structure are suitable. For example, any phenothiazine can be used that has the structure:

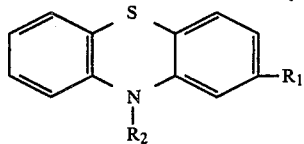

wherein $R_1$ is hydrogen; halogen (chlorine, fluorine, bromine, iodine); haloalkyl (preferably having from one to twenty carbon atoms and fluorine, chlorine, bromine, iodine) such as trifluoromethane; alkyl (preferably having from one to twenty carbon atoms) such as methyl, propyl, hexyl, straight chain, branched, cycloaliphatic, or mixed aliphatic groupings; alkoxy (preferably having from one to twenty carbon atoms) such as methoxy, propoxy, hexoxy; straight chain, branched, or cycloaliphatic, or mixed aliphatic-oxy groupings. If the alkyl group is a straight chain, it is preferred that the number of carbon atoms in the chain should not exceed about five. $R_1$ can also be any other substituent that will not deactivate or hinder the nucleus to the extent that its effect becomes neutralized. $R_2$ can be halogen (fluorine, chlorine, bromine, iodine), an aliphatic group having a terminal nitrogen atom which is preferably a tertiary nitrogen atom such as a dimethylamino group, or any other substituent that will not deactivate or hinder the nucleus to the extent that its effect becomes neutralized. The aliphatic substituent can be straight chained, branched, cyclic, or mixed aliphatic. The aliphatic group can have any number of carbon atoms, but one to twenty atoms are preferred. If the aliphatic group is a straight chain, it is preferred that the number of carbon atoms in the chain should not exceed about five. The aliphatic group can also contain hetero atoms such as oxygen, nitrogen, sulfur and the like and the terminal nitrogen atom can be attached to a chain or it can be contained in a cycloaliphatic ring structure such as piperidine, piperazine, substituted piperidine, substituted piperazone, and the like. Where $R_2$ contains a piperazine ring, either substituted or unsubstituted, the chain need not end in a terminal nitrogen containing group and the piperazine ring may be located anywhere along the aliphatic chain. The number of carbon atoms in the aliphatic chain, however, should not exceed ten.

Some specific examples of suitable phenothiazines that may be used in the practice of the invention include aliphatic, halogenated phenothiazines such as chlorpromazine, triflupromazine, and the like; piperidine phenothiazines such as thioridazine, mesoridazine, piperacetazine, and the like; piperazine phenothiazines such as fluphenazine, trifluoperazine, acetophenazine, carphenazine, fluphenazine, perphenazine, prochlorperazine and the like.

Generally, the phenothiazine can contain any group having the characteristic piperidine or piperazine ring which, in turn, can contain any suitable substituent that will not deactivate or hinder the phenothiazine nucleus to the extent that its effect becomes neutralized, including any suitable substituent disclosed above for $R_1$.

Some specific examples of suitable phenothiazines that may be used in the practice of the invention include aliphatic, halogenated phenothiazines such as chlorpromazine, triflupromazine, and the like; piperidine phenothiazines such as thioridazine, mesoridazine, piperacetazine, and the like; piperazine phenothiazines such as fluphenazine, trifluoperazine, acetophenazine, carphenazine, fluphenazine, perphenazine, prochlorperazine and the like.

Neuroleptic drugs such as thioxanthenes including chlorprothixene, thiothixene and the like; diphenylbutylpiperidines such as pimozide, penfluridol and the like; dibenzoxazepines including loxapine and the like; dibenzodiazepines including clozapine and the like; benzamides such as sulpiride and the like; and butyrophenones including haloperidol and the like; dopamine b-hydroxylase blockers such as disulfiram and mixtures of any of the dopamine receptor blockers can also be used. Haloperidol and chlorpromazine are preferred.

Salts of dopamine receptor blockers can also be used and are preferred since the salt form facilitates the action of the dopamine receptor blocker by increasing its solubility, particularly in lipids and aqueous media, increasing its duration of action, and so on. Some such suitable salts that may be employed include the hydrochloride, methanesulfonate, besylate, maleate, decanoate, enanthate, succinate, lactate, sulfate, quaternary ammonium and any other salt grouping that might be selected by one skilled in the art. Examples of some suitable dopamine receptor blocker salts include chlorpromazine hydrochloride, mesoridazine besylate, acetophenazine maleate, fluphenazine decanoate, fluphenazine enanthate, prochlorperazine maleate, loxapine succinate, haloperidol lactate, haloperidol decanoate, and the like and mixtures thereof.

Dopamine receptor agonists and mixtures of them with each other and/or any of the dopamine receptor blockers can also be used. Any suitable dopamine receptor agonist can be used in the practice of this invention, including amantadine, bromocriptine, piribidil, apomorphine, lisuride, pergolide, mesulergine, and the like. Salts of dopamine receptor agonists can also be used and are preferred for the reasons given above. The dopamine receptor agonists can be in the same salt forms suggested above for the dopamine receptor blockers. Examples of some suitable dopamine receptor agonist salts include amantadine hydrochloride, bromocriptine mesylate, apomorphine hydrobromide, and the like and mixtures thereof.

The amount of the kappa receptor agonist and the amount of the drug acting on dopamine receptors should be chosen from the range of doses for each member of the combination of this invention that individually produces a fall in body temperature ranging from 0.0° C. to 6.0° C. at normal ambient temperature. The particular amount and ratio of each drug in the combination as well as the amount of the combined drugs to be used must be determined empirically and will depend in part on the strength and purity of the compounds used in the combination and the physiological characteristics of the subject. For humans it has been estimated that doses that range generally from about one tenth of a milligram to about five grams of the kappa opioid agonist and from about one milligram to about three grams of the dopamine blocker or dopamine agonist are effective. Also, it is expected that the unique drug combination of this invention is more efficient when administered subcutaneously or intravenously than when administered orally. Consequently, lower dosages can be employed in the former two cases to provide results equivalent to those obtained with higher dosages administered orally.

The amount of the unique combination of drugs of this invention to be administered in any given case must be determined from the subject's anatomical and physiological makeup as well as the subject's response to each of the drugs used and their combination. As is well known in pharmacology and clinical medicine, individual variations occur in response to any given drug or drug combination. This variation is a consequence of such diverse factors as diet, environmental chemicals, genetics, age, disease, and so on. As a result, there may be increased or decreased responses to therapeutic effects of a drug and/or its possible side effects. The effects of one or all drugs in a combination may be altered such that a generally useful combination may become more or less potent and more or less toxic than might be predicted for an individual patient or subject. Sound therapeutic practice calls for individualization of drug dosage and the use of two or more drugs adds to the complexity of individualization of drug therapy. (See also, in this regard Goodman et al, *The Pharmacological Basis of Therapeutics*, 7th edition, 1985, MacMillan, New York) Further, the particular amount and ratio of each drug in the combination as well as the amount of the combined drugs to be used are further dependent on the desired duration of the effect and the desired drop in body temperature at the chosen ambient temperature. The optimum amount of each drug to be used, the timing of administration so that peak effects of both drugs coincide, the ratio of the drugs to one another, and the total dosage of the combination of the drugs at any particular ambient temperature are determined empirically but readily by one skilled in the art given the disclosure herein.

Any of the drugs and combinations suggested herein will provide synergistic results in accordance with this invention within the guidelines set out herein. For example, using U-50 and chlorpromazine at an ambient temperature of about 20° C., weight ratios (mg/kg body weight) of U-50 to chlorpromazine ranging from about 4:1 to 40:1 (or from about 4 to about 40 parts of U-50 per part of chlorpromaine) are advantageously employed.

In another embodiment of this invention, the synergistic combination of drugs defined herein is employed in combination with a mu opioid receptor antagonist in order to enhance the activity of the kappa receptor agonist. This occurs as a result of the activity of an effective amount of an opioid antagonist drug to selectively block or reverse any agonist activity that the kappa receptor agonist may have at a mu receptor site or sites. For example, by titrating the dosage of an antagonist drug such as naloxone, naltrexone, levallorphan methyl iodide salts (as defined hereinbefore) thereof and the like which have greater selectivity for the hyperthermic mu receptors than other receptor types, the mu-receptor agonist properties of a drug having agonist actions at both the mu and kappa receptors can be blocked or reversed with minimal effect on the kappa agonist activity of the drug. An illustration of this would be the use of naloxone hydrochloride, an opioid antagonist more selective for mu than kappa receptors, given along with ethylketazocine methanesulfonate and chlorpromazine hydrochloride to cause an even greater drop in body temperature and less sedation than the combination of the latter two drugs alone. While the specific amount of the mu opioid receptor antagonist should be determined on a case-by-case basis depending on all the variables discussed hereinbefore and the activity of the kappa opioid receptor agonist, it has been estimated generally that amounts in a range of from about fifty micrograms to about a gram of the mu receptor antagonist should suffice.

On the other hand, should it be desired to shorten the duration of the hypothermia or partially reverse poikilothermia such as, for example, when neuroleptanalgesia is employed in surgery and it is desired to shorten the duration of anesthesia, antagonist drugs can be administered such as naloxone, naltrexone, their salts and the like. Alternatively, should a patient experience an unforseen and/or unanticipated side reaction or drug overdosage, antagonist drugs can be administered to block or reverse the effect of the drugs of this invention. In the case of kappa agonists with mu activity, larger doses (about ten times normal) of the antagonist might be required.

The invention is further illustrated but is not intended to be limited by the following examples in which all parts and percentages are by weight unless otherwise specified.

EXAMPLES

Hypothermia Effect

Young adult male Sprague-Dawley rats (Zivic Miller) (200–325 g) are housed in groups of six to a cage in animal quarters maintained at 22°±2° C. and approximately 50% relative humidity for at least one week. Lights are on from 0700 to 1900 hours and food and water are available ad libitum except during testing.

During the experiments, the rates are kept in individual cages in an environmental room at 20°±0.3° C. and 55±5% relative humidity. After a twenty minute adaptation period, temperatures are taken by inserting a thermistor probe approximately 7 cm into the rectum. The rat is held lightly at the base of the tail but is otherwise allowed free movement. Temperatures are read from a digital display thermometer. The first three readings are taken at thirty minute intervals, with the first disregarded to allow for adaptation, and the second and third averaged for a baseline. Immediately after the third reading, rats are given dorsal injections of chlorpromazine hydrochloride (CPZ), 2.5 to 5 mg/kg subcutaneously, or U-50 (U), 20 to 80 mg/kg subcutaneously, either alone or in various combinations, or saline. Readings are taken at 30, 60, 90, 120, 180, 240, and 300 minutes. In some cases, measurements are made at 360 and 420 minutes and at 24 and 48 hours. In the naloxone study, injections of naloxone hydrochloride (10 mg/kg subcutaneously) or saline (control) are given at 0 and 60 minutes. All drugs are dissolved in 0.9% saline on the day of testing and doses are reported as the hydrochloride or methanesulfonate salt.

The results of the experiments are recorded in TABLE I in which the dosages are mg/kg of body weight of the animals. TABLE I shows the synergistic effect of the combination of this invention in terms of the degree and duration of the hypothermia compared to the effect of the individual drugs.

given trifluoperazine have an average maximum temperature drop of 0.1° C. In combination, the drugs produced a maximum drop of 3.7° C. at two hours after injection.

In a similar study, the rats are injected with 80 mg/kg of U-50 and, one hour later, with 1 mg/kg apomorphine. Controls receive saline. Rats given U-50 alone have an average maximum temperature drop of 2.2° C.; those given apomorphine experience an average temperature drop of about 1.8° C. In combination, the drugs of this invention induce a maximum decrease in temperature of 5.2° C. measured at one hour after the injection of the apomorphine.

In another example, haloperidol in a dose of 2 mg/kg causes a slight (0.3° C.) increase in temperature when given alone. In combination with 80 mg/kg of U-50, however, a decrease of 4° C. at two hours after drug administration is achieved.

Poikilothermia Effect

TABLE I

| HYPOTHERMIA EFFECT EXPRESSED AS AREA UNDER THE CURVE (FIGURE) | | |
|---|---|---|
| Drug & Dose (MG/KG) | Mean Area of Time-Effect Curve (0 To 300 Min) Drug(s) Alone (°C.-Min) | Mean Area of Time-Effect Curve (0 to 300 Min) Drug(s) + Naloxone (°C.-Min) |
| SALINE | −91.2 | −18.5 |
| CPZ(2.5) | −157.2 | 14.1* |
| CPZ(5.0) | −409.2 | −178.1* |
| U(20) | −87.5 | — |
| U(40) | −206.6 | 96.9 |
| U(80) | −425.7 | −109.1* |
| CPZ(2.5) + U(20) | −828.6 | −314.6* |
| CPZ(2.5) + U(40) | −1035.9 | −216.3* |
| CPZ(2.5) + U(80) | −1076.9 | −392.4* |
| CPZ(5.0) + U(20) | −688.7 | −558.9 |
| CPZ(5.0) + U(40) | −872.4 | −321.0* |
| CPZ(5.0) + U(80) | −1699.1 | — |

*Significantly different from group without naloxone, $p. < 0.05$, Student's t-test, 2 tailed.

As shown in the Figure, chlorpromazine administered alone produces a fall in body temperature with a maximum of about 2° C. at the 5 mg/kg dose. The effect of U-50 is dose-related with a maximum fall of just over 2° C. at the 80 mg/kg dose. The peak action for CPZ occurs at about 120 minutes, and that for U-50 at approximately 180 minutes. When the two drugs are combined, there is a dramatic potentiation of the hypothermia. The average temperature reduction amounts to more than 8° C. with the 5 mg/kg dose of CPZ and the 80 mg/kg dose of U-50. (Since the mean temperature was still decreasing at five hours but was returning to normal by 24 hours after administration of the drugs, the decrease recorded may not have constituted the true maximum.)

As for the duration of the action, the chlorpromazine induced hypothermia is still present at five hours in 40% of the rats. The hypothermic action of U-50 (40 mg/kg) alone lasts for four to five hours and is still marked at five hours only with the highest dose. In none of the animals receiving a combination of the drugs does the temperature return to baseline at five hours. Recovery is gradual and there are no deaths. When naloxone (10 mg/kg subcutaneously) is administered, at least a partial block of the hypothermia is achieved. In addition, sedation, flaccidity and any other secondary effects are reduced or abolished.

The above experiment is repeated using 2 mg/kg trifluoperazine dihydrochloride and 80 mg/kg U-50. Controls receive saline. Animals given U-50 -alone have an average maximum temperature drop of 2.2° C.; those Young adult male Sprague-Dawley rats (Zivic Miller) (200–325 g) are housed in groups of six to a cage in animal quarters maintained at 22°±2° C. and approximately 50% relative humidity for at least one week prior to testing. Lights are on twelve hours a day, from 0700 to 1900 hours and food and water are available ad libitum except during testing.

During the experiment, the rats are kept in individual metal cages in a controlled environmental chamber at 20°±0.3° C. and 55±5% relative humidity. After allowing twenty minutes for adaptation, temperatures are taken by means of a rectal probe. During this measurement, the rat is held lightly at the base of the tail but is otherwise allowed free movement. Prior to drug injection, three readings are taken at half hour intervals. The first measurement is disregarded to allow for adaptation, and the second two are averaged to establish a baseline body temperature. Directly following the third measurement, the animals are injected dorsally with the drug combination of this invention, subcutaneously. Controls received saline. All drugs are dissolved in 0.9% saline on the day of testing and doses are reported as the hydrochloride or methanesulfonate salt Temperature and behavior are recorded every half hour for the first two hours and every hour thereafter for at least three additional hours.

The poikilothermia effect of the synergistic drug combination of this invention is illustrated in TABLE II. The experiments are carried out as outlined above using 80 mg/kg of U-50 and 5 mg/kg CPZ. The ambient temperatures listed are maintained constant within ±0.1° C. using a constant temperature room. The fact that the body temperature of the subjects tends to approach that of the environment at several different ambient temperatures shows that they have lost the ability to regulate their own body temperature (thermoregulation). At extreme temperatures, the subjects expire because their body temperatures drift passively beyond life-supporting limits. As a consequence, the use of the drug combination of this invention at ambient temperatures beyond the range that will support life (about 18°–29° C.) should be avoided unless measures are taken to prevent mortality. It has been found that no deaths occur at normal ambient temperatures.

TABLE II

| EFFECT OF AMBIENT TEMPERATURE | | | | | |
|---|---|---|---|---|---|
| AMBIENT TEM (°C.) | 5 | 12 | 20 | 30 | 35 |
| CONTROL TEMP. (°C.) MEAN ± S.E.M.* | 37.03 ± .05 | 37.45 ± .28 | 37.43 ± .09 | 37.90 ± .15 | 39.83 ± .17 |
| MAX. TEMP. CHANGE (°C.) MEAN ± S.E.M. | −18.13 ± .51 | −14.13 ± 3.92 | −8.20 ± .69 | 0.93 ± .57 | 2.30 ± .42 |
| TIME OF MAX. CHANGE (MIN) | +180 | +420 | +300 | +180 | +60 |
| DEATHS (%) | 100 | 75 | 0 | 25 | 100 |

*Four animals in each test group.

DESCRIPTION OF THE FIGURE

The FIGURE is a plot of the hypothermia effect of chloroprozine ("CPZ") at 5 mg/kg. dosage, U-50 ("U") at 80 mg/kg. dosage, and the same drugs in combination, demonstrating the synergistic effect of the combination.

It is to be understood that any members of the classes of drugs mentioned as suitable herein can be substituted for its counterpart in the foregoing examples to provide the synergistic effect of this invention. Further, any of the concentrations or dosages, ratios, and conditions mentioned as suitable herein can be substituted for its counterpart in the foregoing examples to provide the unique result of this invention. Therefore, although the invention has been described in considerable detail in the foregoing, such detail is solely for the purpose of illustration. Variations can be made in the invention by those skilled in the art without departing from the spirit and scope of the invention except as set forth in the claims.

What is claimed is:

1. A combination comprising from about 0.1 milligram to about 5 grams of a kappa opioid receptor agonist selected from the group consisting of a bremazocine, nalorphine, ketazocine, tifluadom, trans-3,4-dichloro-N-methyl-N-[1-(1-pyrrolidinyl)cyclohexyl]-benzeneacetamide, (5a,7a,8B)-N-methyl-N-[7-(1-pyrrolidinyl)-1-oxaspiro-(4,5)-dec-8-yl]benzeneacetamide, salts thereof, and mixtures thereof and from about 1 milligram to about 3 grams of a dopamine receptor blocker having the structure:

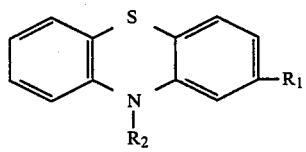

wherein $R_1$ is hydrogen, halogen, haloalkyl, alkyl, or alkoxy; and $R_2$ is halogen, an aliphatic group having a terminal tertiary amino nitrogen group, an aliphatic group having a terminal piperidine substituent, or an aliphatic group having a piperazine substituent, said combination being effective to produce hypothermia or poikilothermia.

2. The combination of claim 1 wherein the kappa opioid receptor agonist is selected from the group consisting of trans-3,4-dichloro-N-methyl-N-[1-(1-pyrrolidinyl)cyclohexyl]benzeneacetamide, (5a,7a,8B)-N-methyl-N-[7-(1-pyrrolidinyl)-1-oxaspiro(4,5)-dec-8-yl]benzeneacetamide, salts thereof, and mixtures thereof.

3. The combination of claim 1 wherein $R_1$ of the dopamine receptor blocker is an alkyl group containing one to twenty carbon atoms.

4. The combination of claim 3 wherein the alkyl group is a straight chain of one to five carbon atoms.

5. The combination of claim 1 wherein $R_2$ of the dopamine receptor blocker is an aliphatic group containing one to twenty carbon atoms.

6. The combination of claim 5 wherein the aliphatic group is a straight chain of one to five carbon atoms.

7. The combination of claim 1 wherein the dopamine receptor blocker is a phenothiazine, salts thereof, and mixtures thereof.

8. The combination of claim 1 wherein the dopamine receptor blocker is selected from the group consisting of a chlorpromazine, thioridazine, fluphenazine, salts thereof and mixtures thereof.

9. The combination of claim 8 wherein the dopamine receptor blocker is chlorpromazine, salts thereof, and mixtures thereof.

10. The combination of claim 1 containing from about 4 to about 40 parts of trans-3,4-dichloro-N-methyl-N-[2-(1-pyrrolidinyl)cyclohexyl]benzeneacetamide per part of chlorpromazine.

11. A method for inducing hypothermia or poikilothermia which comprises administering to a human or animal to produce hypothermia or poikilothermia a combination comprising from about 0.1 milligram to about 5 grams of a kappa opioid receptor agonist selected from the group consisting of a bremazocine, nalorphine, ketazocine, tifluadom, trans-3,4-dichloro-N-methyl-N-(1-(1-pyrrolidinyl)cyclohexyl]benzeneacetamide, (5a,7a,8B)-N-methyl-N-[7-(1-pyrrolidinyl)-1-oxaspiro-(4,5)-dec-8-yl]benzeneacetamide, salts thereof, and mixtures thereof and from about 1 milligram to about 3 grams of a dopamine receptor blocker and mixtures thereof having the structure:

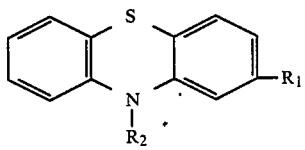

wherein $R_1$ is hydrogen, halogen, haloalkyl, alkyl, or alkoxy; and $R_2$ is halogen, an aliphatic group having a terminal tertiary amino nitrogen group, an aliphatic group having a terminal piperidine substituent, or an aliphatic group having a piperazine substituent.

12. The method of claim 11 wherein hypothermia is induced.

13. The method of claim 12 wherein the combination contains trans-3,4-dichloro-N-methyl-N-[1-(1-pyrrolidinyl)-cyclohexyl]benzeneacetamide or (5a,7a,8B)-methyl-[7-(1-pyrrolidinyl)-1-oxaspiro(4,5)-dec-8-yl]benzeneacetamide.

14. The method of claim 12 wherein the combination contains a phenothiazine.

15. The method of claim 14 wherein the combination contains a dopamine receptor blocker selected from the group consisting of chlorpromazine, thioridazine, fluphenazine, and mixtures thereof.

16. The method of claim 15 wherein the dopamine receptor blocker is chlorpromazine.

17. The method of claim 11 wherein poikilothermia is induced.

18. The method of claim 17 wherein the combination contains trans-3,4-dichloro-N-methyl-N-[1-(1-pyrrolidinyl)cyclohexyl]benzeneacetamide or (5a,7a,8B)-methyl-[7-(1-pyrrolidinyl)-1-oxaspiro(4,5)-dec-8-yl]benzeneacetamide.

19. The method of claim 17 wherein the combination contains a phenothiazine.

20. The method of claim 19 wherein the combination contains a dopamine receptor blocker selected from the group consisting of chlorpromazine, thioridazine, fluphenazine, and mixtures thereof.

21. The method of claim 20 wherein the dopamine receptor blocker is chlorpromazine.

22. The method of claim 11 wherein the combination contains from about 4 to about 40 parts of trans-3,4-dichloro-N-methyl-N-[2-(1-pyrrolidinyl)cyclohexyl]-benzeneacetamide per part of chlorpromazine.

* * * * *